(12) United States Patent
Wariar

(10) Patent No.: US 8,457,761 B2
(45) Date of Patent: Jun. 4, 2013

(54) SYSTEM AND METHOD FOR PROMOTING DIURESIS AND NATRIURESIS BY THE APPLICATION OF ELECTRIC FIELDS TO THE KIDNEY

(75) Inventor: Ramesh Wariar, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 691 days.

(21) Appl. No.: 12/683,553

(22) Filed: Jan. 7, 2010

(65) Prior Publication Data

US 2010/0179620 A1 Jul. 15, 2010

Related U.S. Application Data

(60) Provisional application No. 61/144,500, filed on Jan. 14, 2009.

(51) Int. Cl.
*A61N 1/00* (2006.01)
(52) U.S. Cl.
USPC ............................................................ 607/68
(58) Field of Classification Search
USPC ............................................................ 607/68
See application file for complete search history.

(56) References Cited

U.S. PATENT DOCUMENTS

| 5,529,574 | A | 6/1996 | Frackelton |
| 5,779,661 | A | 7/1998 | Stephen et al. |
| 6,381,493 | B1 | 4/2002 | Stadler et al. |
| 6,424,864 | B1 | 7/2002 | Matsuura |
| 6,941,172 | B2 | 9/2005 | Nachum |
| 6,978,174 | B2 | 12/2005 | Gelfand et al. |
| 2003/0216792 | A1 | 11/2003 | Levin et al. |
| 2004/0220621 | A1 | 11/2004 | Zhou et al. |
| 2005/0021092 | A1 | 1/2005 | Yun et al. |
| 2005/0187581 | A1 | 8/2005 | Hara et al. |
| 2005/0192638 | A1 | 9/2005 | Gelfand et al. |
| 2005/0228459 | A1 | 10/2005 | Levin et al. |
| 2005/0228460 | A1 | 10/2005 | Levin et al. |
| 2005/0234523 | A1 | 10/2005 | Levin et al. |
| 2005/0288730 | A1 | 12/2005 | Deem et al. |
| 2006/0025821 | A1 | 2/2006 | Gelfand et al. |

(Continued)

FOREIGN PATENT DOCUMENTS

| WO | WO-0074775 A1 | 12/2000 |
| WO | WO-0152931 A1 | 7/2001 |

(Continued)

OTHER PUBLICATIONS

"European Application Serial No. 07862119,0, Communication mailed Feb. 28, 2012", 39 pgs.

(Continued)

*Primary Examiner* — Christopher D Koharski
*Assistant Examiner* — Nadia Ahmad
(74) *Attorney, Agent, or Firm* — Schwegman Lundberg & Woessner, P.A.

(57) ABSTRACT

A system and method of applying an electric field to the kidney of a subject can reduce renal salt and water retention through the process of electrophoresis. The system includes a first and a second electrode, at least of which is implantably associated with the kidney. The electric field can be controlled to affect the removal of a first constituent (e.g. sodium) from the kidney while the level of a second constituent (e.g. potassium) is maintained within normal physiological range.

22 Claims, 5 Drawing Sheets

U.S. PATENT DOCUMENTS

| | | | |
|---|---|---|---|
| 2006/0041277 | A1 | 2/2006 | Deem et al. |
| 2006/0142801 | A1 | 6/2006 | Demarais et al. |
| 2006/0206150 | A1 | 9/2006 | Demarais et al. |
| 2006/0212076 | A1 | 9/2006 | Demarais et al. |
| 2006/0212078 | A1 | 9/2006 | Demarais et al. |
| 2006/0235474 | A1 | 10/2006 | Demarais |
| 2006/0265014 | A1 | 11/2006 | Demarais et al. |
| 2006/0265015 | A1 | 11/2006 | Demarais et al. |
| 2006/0276852 | A1 | 12/2006 | Demarais et al. |
| 2007/0066957 | A1 | 3/2007 | Demarais et al. |
| 2007/0083239 | A1 | 4/2007 | Demarais et al. |
| 2007/0129761 | A1 | 6/2007 | Demarais et al. |
| 2007/0203549 | A1 | 8/2007 | Demarais et al. |
| 2007/0265687 | A1 | 11/2007 | Deem et al. |
| 2008/0119907 | A1* | 5/2008 | Stahmann ............... 607/40 |

FOREIGN PATENT DOCUMENTS

| | | |
|---|---|---|
| WO | WO-2006090397 A2 | 8/2006 |
| WO | WO-2007019491 A2 | 2/2007 |
| WO | WO-2008066732 A1 | 6/2008 |
| WO | WO-2010/083086 A1 | 7/2010 |

OTHER PUBLICATIONS

"European Application Serial No. 10700615.7, Office Action mailed Oct. 12, 2011", 2 pgs.

"European Application Serial No. 10700615.7, Response filed Feb. 20, 2012 to Office Action mailed Oct. 12, 2011", 4 pgs.

"U.S. Appl. No. 11/562,436, Non Final Office Action mailed Mar. 10, 2009", 13 pgs.

"U.S. Appl. No. 11/562,436, Response filed Sep. 10, 2009 to Non Final Office Action mailed Mar. 10, 2009", 11 pgs.

"U.S. Appl. No. 11/562,436, Final Office Action mailed Jan. 4, 2010", 13.

"Figure", *Vander's renal physiology* / Douglas C. Eaton, John P. Pooler, New York : Lange Medical Books/McGraw Hill, Health Publishing Division, 6th Edition, (2004), 76.

"PCT Application Serial No. PCT/US2007/024185, International Search Report mailed Apr. 22, 2008", 5 pgs.

"PCT Application Serial No. PCT/US2007/024185, Written Opinion mailed", 9 pgs.

Agre, P., et al., "Aquaporins and ion conductance", *Science*, 275(5305), (Mar. 7, 1997), 1490-1492.

Blank, M., et al., "Frequency dependence of Na,K-ATPase function in magnetic fields", *Bioelectrochemistry and Bioenergetics*, 42(2), (May 1997), 231-234.

Blank, M., et al., "Threshold for inhibition of Na, K-ATPase by ELF alternating currents", *Bioelectromagnetics*, 13(4), (1992), 329-33.

Bogoliubov, V. M, et al., "Electrotherapy of aterial hypertension", *Geneva Foundation for Medical Education and Research*, http://www.gfmer.ch/TMCAM/Hypertension/Electrotherapy_aterial_hypertension.htm, (1996), 3 Pages.

Burkhoff, D., et al., "Electric currents applied during the refractory period can modulate cardiac contractility in vitro and in vivo.", *Heart Fail Rev.*, 6(1), (Jan. 2001), 27-34.

Kinn, A.-C., et al., "Effects of Direct Current on Renal Function", *Urological Research*, 19, (1991), 397-400.

Kverneland, A., et al., "Evidence of changes in renal charge selectivity in patients with type 1 (insulin-dependent) diabetes mellitus", *Diabetologia*, 29(9), (Sep. 1986), 634-9.

Liu, D. S., et al., "Activation of Na+ and K+ Pumping Modes of (Na,K)-ATPase by an Oscillating Electric Field", *The Journal of Biological Chemistry*, 265(13), (May 5, 1990), 7260-7267.

Markin, V. S., et al., "Frequency and concentration windows for the electric activation of a membrane active transport system", *Biophys J.*, 59(6), (Jun. 1991), 1308-16.

Misner, B., "Table from "The Endurolyte Rationale"", http://www.e-caps.com/za/ECP?PAGE=ARTICLE&ARTICLE.ID=770, (2000).

Petrov, A., et al., "Is flexoelectricity the coupling factor between chemical energy and osmotic work in the pump? A model of pump.", *Gen Physiol Biophys.*, 5(4), (Aug. 1986), 391-403.

Rosemberg, Y., et al., "Incorporation of macromolecules into cells and vesicles by low electric field: Induction of endocytotic-like processes", *Bioelectrochemistry and Bioenergetics*, 42(2), (May 1997), 275-281.

Serpersu, E. H., et al., "Activation of Electrogenic Rb+ Transport of (Na,K)-ATPase by an Electric Field", *The Journal of Biological Chemistry*, 259(11), (Jun. 10, 1984), 7155-7162.

Serpersu, E. H., et al., "Stimulation of a ouabain-sensitive Rb+ uptake in human erthrocytes with an external electric field", *J Membr Biol.*, 74(3), (1983), 191-201.

Teissie, J., et al., "Voltage modulation of Na+/K+ transport in human erythrocytes", *J Physiol* (Paris), 77(9), (May 1981), 1043-53.

"U.S. Appl. No. 11/562,436, Final Office Action mailed Jan. 4, 2010", 12 pgs.

"U.S. Appl. No. 11/562,436, Final Office Action mailed Jan. 10, 2011", 14 pgs.

"U.S. Appl. No. 11/562,436, Non final Office Action mailed May 10, 2011", 14 pgs.

"U.S. Appl. No. 11/562,436, Response filed Apr. 11, 2011 to Final Office Action mailed Jan. 10, 2011", 9 pgs.

"U.S. Appl. No. 11/562,436, Response filed Oct. 22, 2010 to Non Final Office Action mailed Jul. 23, 2010", 9 pgs.

"Australian Application Serial No. 2007325818, First Examiner Report mailed Dec. 3, 2010", 3 pgs.

"Australian Application Serial No. 2007325818, Request to Amend a Complete Specification filed Jun. 22, 2011 in Response to First Examanier Report mailed Dec. 3, 2010", 18 pgs.

"European Application Serial No. 07862119.0, Office Action mailed Feb. 17, 2011", 4 pgs.

"European Application Serial No. 07862119.0, Response filed Jun. 24, 2011 to Office Action mailed Feb. 17, 2011", 12 pgs.

"European Application Serial No. 07862119.0, Response Filed Oct. 11, 2010 to Office Action mailed May 31, 2010", 15 pgs.

"International Application Serial No. PCT/US2010/020320, International Preliminary Report on Patentability mailed Jul. 28, 2011", 8 pgs.

"Japanese Application Serial No. 2009-538396, Voluntary Amendment filed Oct. 26, 2010", (English Translation), 3 pgs.

"U.S. Appl. No. 11/562,436, Non-Final Office Action mailed Jul. 23, 2010", 14 pgs.

"U.S. Appl. No. 11/562,436, Response filed Jun. 29, 2010 to Final Office Action mailed Jan. 4, 2010", 10 pgs.

"European Application Serial No. 07862119.0, Office Action mailed May 31, 2010", 4 pgs.

"International Application Serial No. PCT/US2010/020320, International Search Report mailed Mar. 24, 2010", 4 pgs.

"International Application Serial No. PCT/US2010/020320, Written Opinion mailed Mar. 24, 2010", 7 pgs.

Aperia, A., et al., "Activation/deactivation of renal $Na^+,K^+$-ATPase: a final common pathway for regulation of natriuresis.", The FASEB Journal. 8(6), (1994), 436-439.

"Australian Application Serial No. 2010204957, Examiner First Report mailed May 28, 2012", 2 pgs.

* cited by examiner

SYSTEM AND METHOD FOR PROMOTING DIURESIS AND NATRIURESIS BY THE APPLICATION OF ELECTRIC FIELDS TO THE KIDNEY

CROSS-REFERENCE TO RELATED APPLICATION

This application claims the benefit of U.S. Provisional Application No. 61/144,500, filed on Jan. 14, 2009, under 35 U.S.C. §119(e), which is hereby incorporated by reference in its entirety.

BACKGROUND

Heart failure is a complex syndrome resulting from the inability of the heart to pump blood sufficient to meet the body's needs. Heart failure is a progressive disease most common in the elderly and usually caused by other diseases/conditions that gradually damage the heart such as coronary heart disease, damaged heart valves, external pressure around the heart, and cardiac muscle disease. The kidneys play an important role in compensating for the heart's inability to pump blood. Normally, healthy kidneys are responsible for various functions such as: removal of fluid and wastes; maintenance of blood pressure; maintenance of salt, water, electrolyte and acid-base balance; stimulation of red cell production (via the release of erythropoietin); and promotion of calcium absorption. In heart failure patients, the kidneys compensate for inadequate cardiac output by increasing the volume of circulating blood (by increasing sodium and water reabsorption, thereby decreasing urine output), and maintaining blood pressure. In the short term these compensatory mechanisms serve to increase cardiac performance. However in the long term they become maladaptive. Heart failure can lead to progressive renal dysfunction (referred to as "cardiorenal syndrome") that is associated with increased morbidity and mortality. Together, cardiac and renal dysfunction lead to fluid overload, which is often manifested as excess lung fluid (pulmonary edema) and dyspnea.

The primary functional unit of the kidneys is called the "nephron." Each kidney consists of about one million nephrons. In each nephron, a group of interconnected capillary loops, called the glomerulus, filters the blood and produces a fluid, called the filtrate. The filtrate is similar to blood plasma but contains very little total protein. Unlike large proteins (e.g. albumin), inorganic ions and low-molecular-weight organic solutes are freely filtered by the glomerulus into the filtrate. Since the inorganic ions and low-molecular-weight organic solutes are freely filtered, their concentrations in the filtrate are very similar to their concentration in blood plasma.

The filtrate leaving the glomerulus contains a combination of waste materials that need to be removed from the body, other solutes (e.g. electrolytes)—some of which need to be removed from the body and some of which need to be retained by the body, and water—most of which needs to be retained by the body. To affect the removal and retention these substances, the filtrate leaving the glomerulus empties into a tiny tube called a tubule. Several processes occur within the tubule, including filtration, reabsorption, and secretion. These processes affect proper removal and retention of the various solutes and water.

Most of the water and other solutes (e.g. glucose, electrolytes, bicarbonate) are reabsorbed as the filtrate moves though the tubule. The process of reabsorption is critical since without it, the body would quickly dehydrate and suffer electrolyte and pH imbalances. Reabsorption is particularly important in the process of sodium and water retention/excretion. As the filtrate moves through the lumen of the tubule, some positively charged sodium ions passively enter the surrounding tubular cells since the insides of tubular cells are negatively charged with respect to the lumen. After entering the tubular cells, the sodium ions are actively transported out into the interstitial fluid, and eventually reabsorbed back into the blood. The reabsorption of water occurs via osmosis, secondary to the reabsorption of sodium. The sodium and water not reabsorbed by the tubular cells pass through the tubule, along with other solutes (e.g. urea), thus producing urine.

In heart failure patients, decreased cardiac output leads to vasoconstriction and various neurohormonal signals, both of which direct the kidney to reabsorb more sodium and water. This, in turn, leads to fluid overload, as mentioned above. In order to counteract increased sodium and water retention, drugs such as diuretics can be used to block sodium transport or to block the hormonal signals that lead to increased sodium reabsorption. However, many heart failure patients become less responsive to diuretics over time, and diuretics can produce unwanted side effects, such as excess potassium excretion. Thus, it would be valuable to identify a method of diuresis that does not have the unwanted effects of the pharmaceutical diuretics currently available. Promoting diuresis via such an alternative method could benefit heart failure patients suffering from fluid overload, as well as patients suffering from fluid overload due to other etiologies (i.e. renal failure).

OVERVIEW

This document describes, among other things, a system and method of applying an electric field to the kidney of a subject can reduce renal salt and water retention through the process of electrophoresis. The system includes a first and a second electrode, at least of which is implantably associated with the kidney. The electric field can be controlled to affect the removal of a first constituent (e.g. sodium) from the kidney while the level of a second constituent (e.g. potassium) is maintained within normal physiological range.

Example 1 describes a system. In this example, the system comprises a first electrode and a second electrode, wherein at least one of the first electrode or the second electrode is implantably associated with a kidney of a subject; an electric field generator circuit coupled to the first electrode and the second electrode and configured to generate an electric field; and a controller circuit coupled to the electric field generator circuit and configured to control the electric field such that, through a process of electrophoresis, a first constituent is removed from the kidney and a second constituent is maintained within normal physiological range.

In Example 2, the system of Example 1 optionally comprises a monitoring circuit configured to monitor a level of the first constituent in the kidney and a level of the second constituent in the kidney.

In Example 3, the system of one or more of Examples 1-2 optionally comprises the first electrode, including a cathode, located in or near at least one of a Bowman's capsule, a macula densa, a tubule, a collecting duct, a renal pelvis, a ureter, or a urinary bladder.

In Example 4, the system of one or more of Examples 1-3 optionally comprises the second electrode, including an anode, located in or near at least one of a renal vein, a renal artery, or a peritubular capillary network.

In Example 5, the system of one or more of Examples 1-4 optionally comprises first constituent including sodium and the second constituent including potassium.

In Example 6, the system of one or more of Examples 1-5 optionally comprises the controller circuit configured to control the electric field to remove water from the kidney.

In Example 7, the system of one or more of Examples 1-6 optionally comprises the controller circuit configured to control the electric field to treat a condition of the subject including fluid overload.

In Example 8, the system of one or more of Examples 1-7 optionally comprises the electric field generator circuit configured to generate a biphasic voltage pulse comprising a first and a second phase, a magnitude of at least one of the first or the second phase being between about 0.1 Volt and about 20 Volts.

In Example 9, the system of one or more of Examples 1-8 optionally comprises the electric field generator circuit configured to generate pulses at a repetition rate that is between about 10 minutes and about 1 microsecond.

In Example 10, the system of one or more of Examples 1-9 optionally comprises the controller circuit configured to control at least one of a magnitude, a pulsewidth, a frequency, a duration, or a waveform associated with the electric field using information about at least one of the level of the first or the second constituent.

In Example 11, the system of one or more of Examples 1-10 optionally comprises the controller circuit configured to control at least one of a magnitude, a pulsewidth, a frequency, a duration, or a waveform associated with the electric field using information from at least one implanted sensor including an implantable heart sound sensor; an implantable impedance sensor; an implantable activity sensor; an implantable respiration sensor; an implantable blood pressure sensor; an implantable electrocardiogram sensor; an implantable oxygen saturation sensor; an implantable blood flow sensor; an implantable temperature sensor; or an implantable renal conductivity sensor.

Example 12 describes a method. In this example, the method comprises applying an electric field to a subject using a first electrode and a second electrode, at least one of the first electrode or the second electrode being implantably associated with a kidney of the subject; and controlling the electric field such that, through a process of electrophoresis, a first constituent is removed from the kidney and a second constituent is maintained within normal physiological range.

In Example 13, the method of Example 12 optionally comprises monitoring a level of the first constituent in the kidney and a level of the second constituent in the kidney.

In Example 14, the method of one or more of Examples 12-13 optionally comprises applying an electric field using the first electrode, including a cathode, in or near at least one of a Bowman's capsule, a macula densa, a tubule, a collecting duct, a renal pelvis, a ureter, or a urinary bladder.

In Example 15, the method of one or more of Examples 12-14 optionally comprises applying an electric field using the second electrode, including an anode, in or near a renal vein, a renal artery, or a peritubular capillary network.

In Example 16, the method of one or more of Examples 12-15 optionally comprises the first constituent including sodium and the second constituent including potassium.

In Example 17, the method of one or more of Examples 12-16 optionally comprises the controlling the electric field by removing water from the kidney.

In Example 18, the method of one or more of Examples 12-17 optionally comprises removing the water from the kidney to treat a condition of the subject including fluid overload.

In Example 19, the method of one or more of Examples 12-18 optionally comprises applying an electric field by providing a biphasic voltage pulse including a first and a second phase, a magnitude of at least one of the first or the second phase being between about 0.1 Volt and about 20 Volts.

In Example 20, the method of one or more of Examples 12-19 optionally comprises applying an electric field by providing pulses at a repetition rate that is between about 10 minutes and about 1 microsecond.

In Example 21, the method of one or more of Examples 12-20 optionally comprises controlling the electric field by controlling at least one of a magnitude, a pulsewidth, a frequency, a duration, or a waveform associated with the electric field using information about at least one of the level of the first constituent or the second constituent.

In Example 22, the method of one or more of Examples 12-21 optionally comprises controlling the electric field by controlling at least one of a magnitude, a pulsewidth, a frequency, a duration, or a waveform associated with the electric field using information from at least one implanted sensor including an implantable heart sound sensor; an implantable impedance sensor; an implantable activity sensor; an implantable respiration sensor; an implantable blood pressure sensor; an implantable electrocardiogram sensor; an implantable oxygen saturation sensor; an implantable blood flow sensor; an implantable temperature sensor; or an implantable renal conductivity sensor.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals can describe substantially similar components throughout the several views. Like numerals having different letter suffixes can represent different instances of substantially similar components. The drawings illustrate generally, by way of example, but not by way of limitation, various embodiments discussed in the present document.

DETAILED DESCRIPTION

This document describes, among other things, applying electric fields to a patient's kidney(s) to reduce retention of salt and water through a process of electrophoresis. Reduced salt and water retention can benefit patients suffering from fluid overload, such as those with congestive heart failure.

Figure 1:
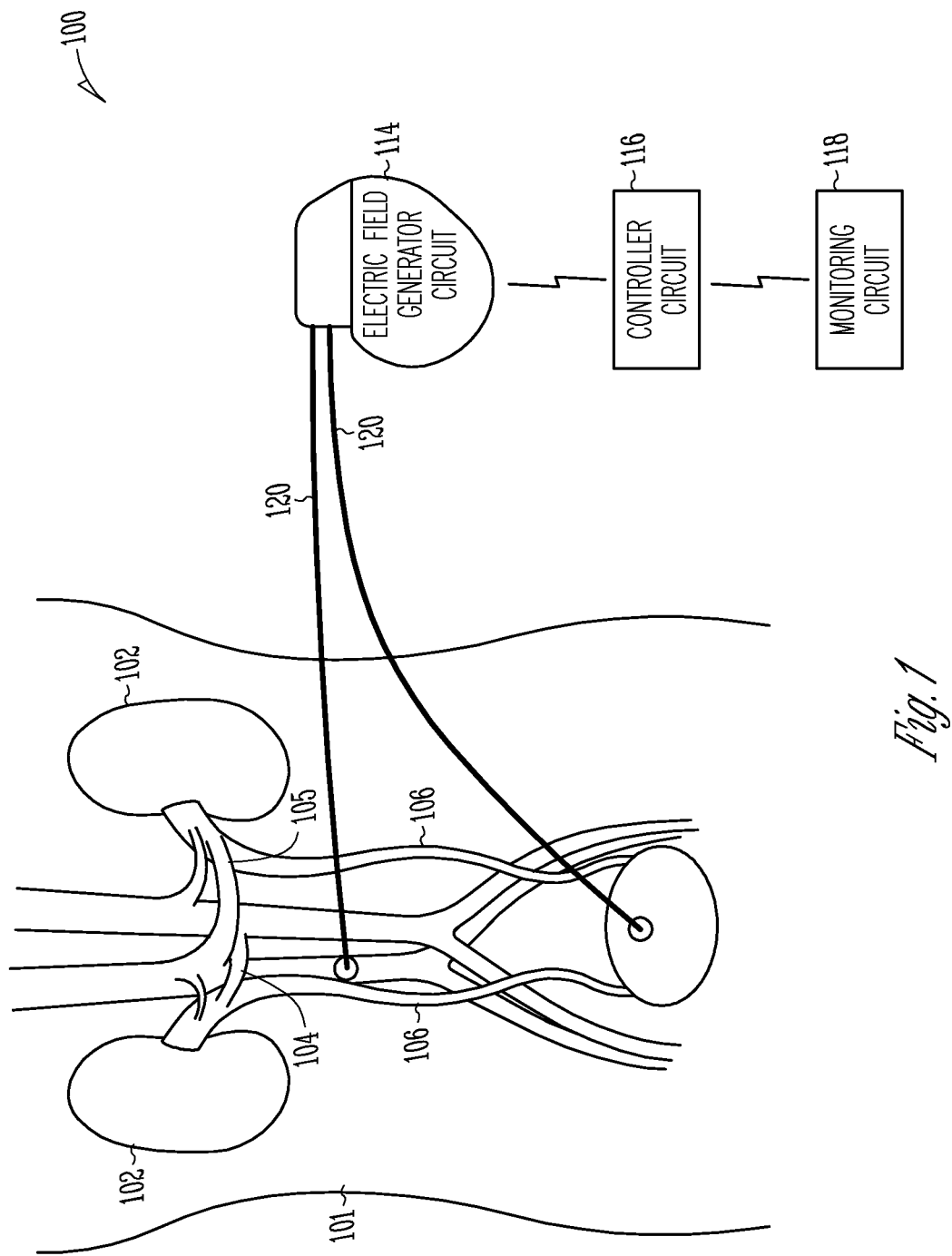
FIG. 1 is a diagram illustrating generally an example of a system for applying an electric field to a subject's kidney.

FIG. 1 is a diagram illustrating generally an example of a system 100 for applying an electric field to a subject's body 101, and more specifically, to one or both kidneys 102. In this example, a first electrode 110 and a second electrode 112 have been implanted in the subject. In certain examples, at least one of the first electrode 110 or second electrode 112 can be incorporated into a stent anchor placed within a vessel or tubular structure, such as a ureter. In other examples, at least one of the first electrode 110 or second electrode 112 can be incorporated into a cuff surrounding a vessel or tubular structure. The first electrode 110, which can include a cathode, is shown implanted in the urinary bladder 108. Although not shown, the first electrode 110 can also be placed in or near a ureter 106, a Bowman's capsule, a macula densa, a renal tubule, a collecting duct, or a renal pelvis (see FIGS. 3 and 4). The second electrode 112, which can include an anode, is shown implanted in a renal vein 104. Alternatively, the second electrode 112 can be placed in or near a renal artery 105 or a peritubular capillary network (see FIGS. 3 and 4). The first electrode 110 and the second electrode 112 are coupled to an electric field generator circuit 114, which can be external, as shown, or part of an implantable device. In certain examples, the first electrode includes the anode and the second electrode includes the cathode. The electrodes 110 and 112 can be coupled to the electric field generator circuit 114 via one or more leads 120, as shown. In certain examples, the leads 120 can be implantable. Alternatively, the electrodes 110 and 112 can be coupled to the electric field generator circuit 114 via leadless technologies.

In certain examples, the electric field generator circuit 114 can generate a biphasic voltage pulse, including, for example, a first positive and a second negative phase. The magnitude of at least one of the first or second phase can be between about 0.1 Volt and about 20 Volts. Also, the electric field generator circuit 114 can generate pulses at a repetition rate that is between about 10 minutes and about 1 microsecond. In certain examples, the electric field generator circuit 114 can produce biphasic pulses in order to produce charge balance in the vicinity of the electrodes while ensuring greater net excretion of sodium and water.

The electric field generator circuit 114 is coupled to the controller circuit 116, which can be external, as shown, or part of an implantable device. In certain examples, the controller circuit 116 can communicate wirelessly with the electric field generator circuit 114. In certain examples, the controller circuit 116 can receive input information from certain implanted sensors, such as a sodium sensor, a potassium sensor, a heart sound sensor, a thoracic impedance sensor, an activity sensor, a respiration sensor, a blood pressure sensor, an electrocardiogram sensor, an oxygen saturation sensor, a blood flow sensor, a temperature sensor, or a renal conductivity sensor. The sensors can be incorporated in the monitoring circuit 118, described below. The sensor input information can be used by the controller circuit 116 to adjust at least one of a magnitude, a pulsewidth, a frequency, a duration, or a waveform associated with the electric field. For example, when the controller circuit 116 receives information from a sodium sensor indicating an abnormally high level of sodium in the renal tubules, the controller circuit 116 can direct the electric field generator circuit 114 to increase the magnitude, pulsewidth, frequency, or duration of electric energy delivered to the kidney. The increased magnitude, pulsewidth, frequency, or duration of electric energy can, in turn, create an electrophoretic gradient causing an increase in sodium and water excretion, as described below.

Figure 5:
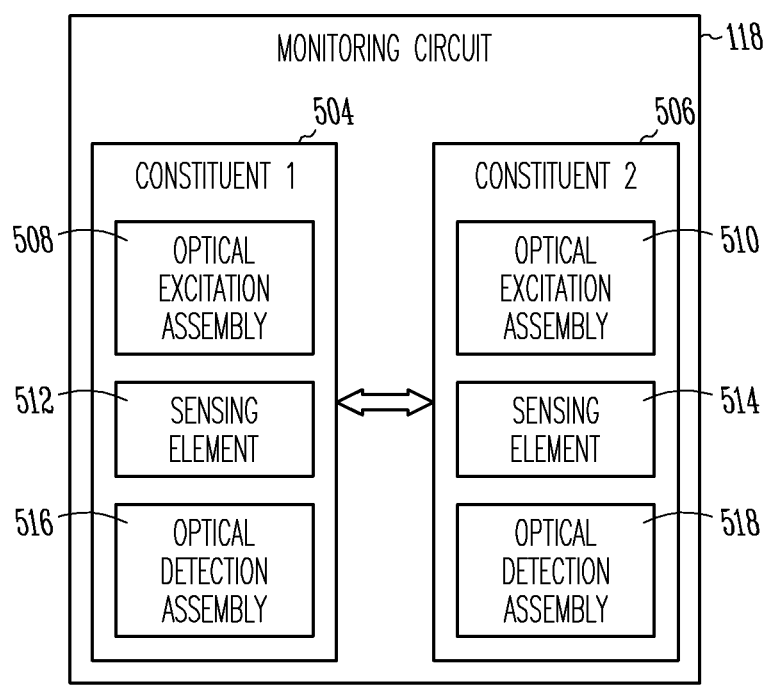
FIG. 5 is a block diagram illustrating generally an example of a monitoring circuit associated with the application of an electric field to the kidney.

The controller circuit 116 is also coupled to the monitoring circuit 118, which can be external, as shown, or part of an implantable device. The monitoring circuit 118, which is described further with regard to FIG. 5, is configured to monitor the level of a first constituent in the kidney and a level of a second constituent in the kidney. For example, the first constituent may include sodium and the second constituent may include potassium, and the monitoring circuit 118 includes a sodium sensor and a potassium sensor to monitor the levels of the first and second constituents.

In certain examples, the monitoring circuit 118 can communicate wirelessly with the controller circuit 116. Information from the monitoring circuit 118 about the levels of a first and second constituent in the kidney can be used by the controller circuit to adjust the magnitude, pulsewidth, frequency, or duration of electric energy delivered to the kidney, such that the levels of the first and second constituents remain within specified ranges.

Figure 2:
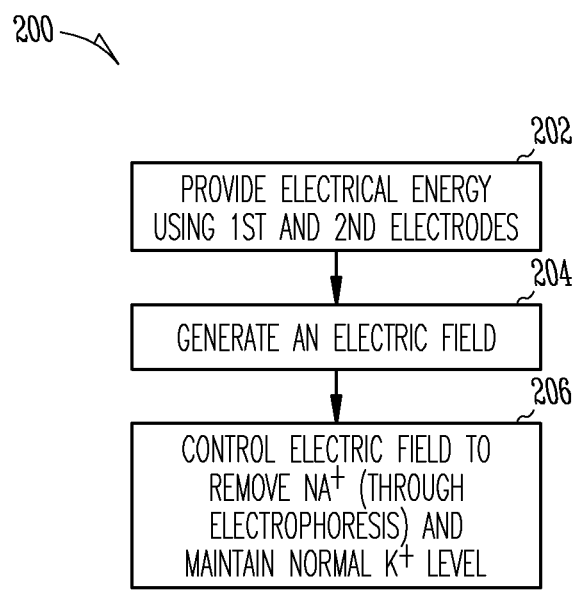
FIG. 2 is a flow chart illustrating an overview of a method for providing electrical energy to the kidney of a subject to control, through a process of electrophoresis, the levels of a first and second constituent in the kidney.

FIG. 2 is a flow chart illustrating an overview of a method 200 for providing electrical energy to the kidney of a subject to control, through a process of electrophoresis, the levels of a first and second constituent in the kidney. At 202, electrical energy is provided using a first electrode and a second electrode. At least one of the first electrode or the second electrode is implantably associated with a kidney of a subject. In certain examples, the first electrode can include a cathode and it can be used in or near at least one of a Bowman's capsule, a macula densa, a tubule, a collecting duct, a renal pelvis, a ureter, or a urinary bladder. In certain examples, the second electrode can include an anode, and it can be used in or near a renal vein, renal artery, or a peritubular capillary network. Providing electrical energy using the first and second electrodes can include providing a biphasic voltage pulse. At least one of the first or second phases of the biphasic voltage pulse can have a magnitude in the range of about 0.1-20 Volts. Furthermore, providing electrical energy using the first and second electrodes can include providing pulses at a repetition rate in the range of about 1 microsecond to about 10 minutes.

At 204, an electric field is generated using the first and second electrodes. At 206, the electric field is controlled such that, through a process of electrophoresis, a first constituent, such as sodium, is removed from the kidney and a second constituent, such as potassium, is maintained within normal physiological levels. In certain examples, the levels of the first and second constituents can be monitored through an implanted or external sensing device. Initiating electrophoresis with the electric field can further include removing water from the kidney, for example when the first constituent includes sodium. When sodium ions are removed from the kidney, water passively diffuses down its concentration gradient, out of the kidney and into the filtrate, along with sodium. Controlling the electric filed can also include controlling at least one of a magnitude, a pulsewidth, a frequency, a duration, or a waveform associated with the electric field using information about at least one of the level of the first constituent or the second constituent. Similarly, in certain examples controlling the electric field can include controlling at least one of a magnitude, a pulsewidth, a frequency, a duration, or a waveform associated with the electric field using information from at least one implanted sensor including an implantable heart sound sensor; an implantable impedance sensor; an implantable activity sensor; an implantable respiration sensor; an implantable blood pressure sensor; an implantable electrocardiogram sensor; an implantable oxygen saturation sensor; an implantable blood flow sensor; an implantable temperature sensor; or an implantable renal conductivity sensor.

Figure 3:
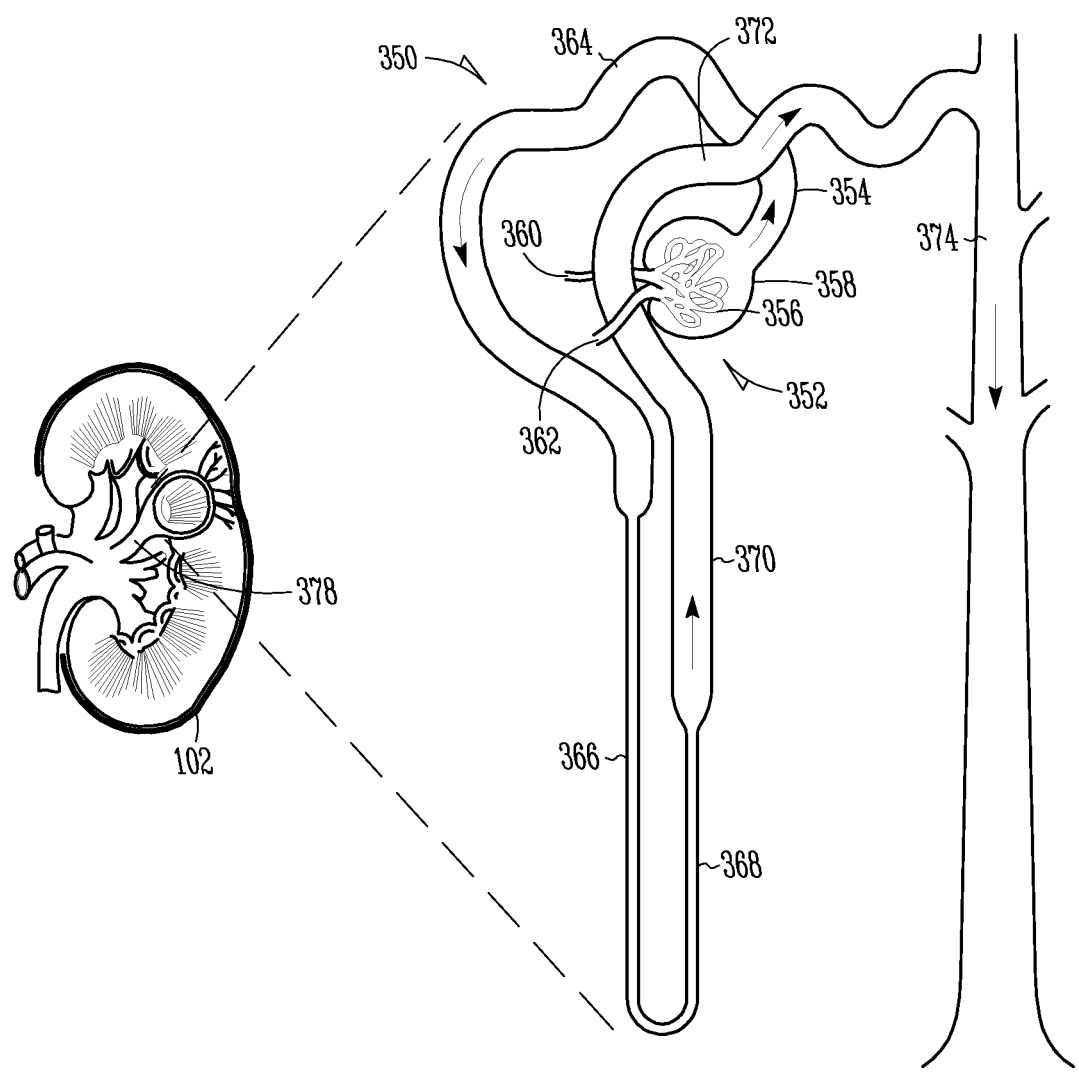
FIG. 3 is a diagram illustrating generally an example of a nephron in a kidney.

FIG. 3 diagrammatically illustrates one of many nephrons 350 in a kidney 102. As discussed above, the nephrons 350 perform the actual filtering in the kidneys 102. For better understanding of how the present subject matter may be used to affect renal salt and water excretion, discussion will now turn to the normal physiology of a nephron 350 and its associated structure.

Each nephron consists of a spherical filtering component, called the renal corpuscle 352, and a tubule 354 extending from the renal corpuscle 352. The renal corpuscle 352 is responsible for the initial step in urine formation (i.e., the separation of a protein-free filtrate from plasma) and consists of interconnected capillary loops, called the glomerulus 356, surrounded by a hollow capsule, known as Bowman's capsule 358. Blood enters and leaves Bowman's capsule 358 through afferent and efferent arterioles 360, 362 that penetrate the surface of the capsule 358. A fluid-filled space exists within the capsule 358, and it is into this space that fluid filters. The fluid filtered from the glomerulus 356 into the capsule 358 is called the filtrate. Opposite the vascular pole, the Bowman's capsule 358 has an opening that leads into the first portion of the tubule 354. As the filtrate continues to flow through the various portions of the tubule (the proximal convoluted tubule 364, the descending thin limb of Henle's loop 366, the ascending thin limb of Henle's loop 368, the think ascending limb of Henle's loop, the distal convoluted tubule 372, and the collecting duct 374), the processes of tubular reabsorption (e.g. reabsorption of sodium, water, bicarbonate, glucose, amino acids, phosphate, etc.) and tubular secretion (e.g. secretion of urea, hydrogen ions, and other waste products) continue until the filtrate (now urine) enters the renal calyx 378. Each renal calyx is continuous with the ureter 106 (FIG. 1), which empties into the urinary bladder 108 (FIG. 1), where urine is temporarily stored and from which it is intermittently eliminated.

Figure 4:
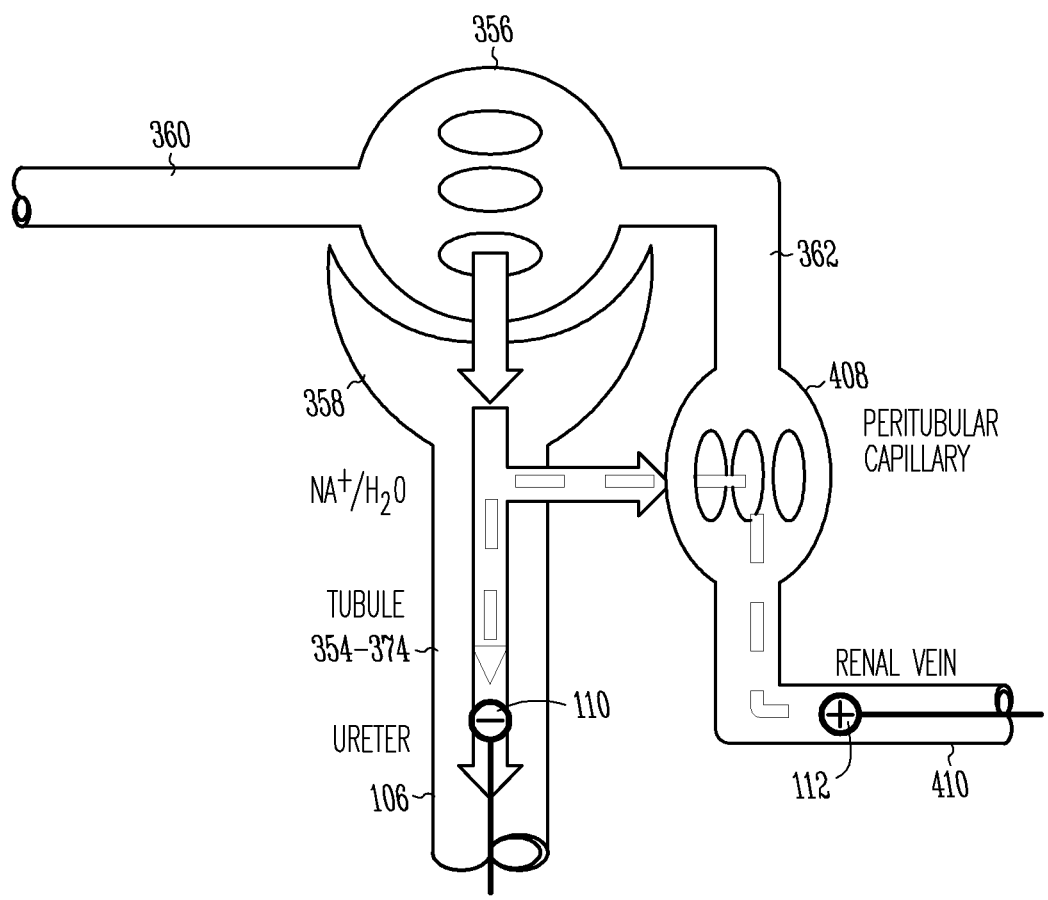
FIG. 4 is a diagram illustrating generally an example of some of the processes that take place within a nephron.

FIG. 4 is a simplified diagram further illustrating some of the processes that take place in the nephron, as described in FIG. 3. As blood enters the glomerulus 356 through the afferent arteriole 360, inorganic ions (e.g. sodium), low-molecular-weight organic solutes, and water are freely filtered from the blood into the fluid-filled space of the Bowman's capsule 358. Normally, about 20% of the blood plasma entering the glomerulus 356 is filtered from the glomerulus 356 into the Bowman's capsule 358. The remaining blood exits the glomerulus 356 through the efferent arteriole 362, which then subdivides into a set of peritubular capillaries 408. The peritubular capillaries 408 then rejoin to form veins, and ultimately the renal vein 410, through which blood leaves the kidney.

The portion of the blood that is filtered from the glomerulus 356 into the Bowman's capsule 358 forms the filtrate, as discussed above. The filtrate includes small ions, glucose, urea, amino acids, hormones, some macromolecules, and water. As discussed above with respect to FIG. 3, many of the substances in the filtrate will later be reabsorbed in the tubule 354-374. The discussion will now focus on the reabsorption of sodium and water from lumen of the tubule 354-374 into the peritubular capillary 408. Positively charged sodium ions in the tubular lumen passively enter the cells that form the wall of the tubule 354-374 (tubular cells), as the insides of tubular cells are negatively charged with respect to the lumen. After entering the tubular cells, the sodium ions are actively transported out into the interstitial fluid, and eventually reabsorbed back into the blood through the peritubular capillary 408. The reabsorption of water from the tubule into the peritubular capillary 408 occurs via osmosis, secondary to the reabsorption of sodium.

When a negatively charged electrode or anode 110 is placed in the ureter 106 and a positively charged electrode or cathode 112 is placed in the renal vein 410, as shown, the resulting electric field can affect the reabsorption of sodium and water through the process of electrophoresis. Application of an electric field to charged particles (e.g. sodium ions) dispersed in a fluid causes the particles to migrate along their electrophoretic gradient. Applying the above described electric field to the kidney can cause sodium to migrate along its electrophoretic gradient from the positively charged peritubular capillary 408 to the negatively charged ureter 106 (and adjacent tubule 354-374), counteracting the passive transport of positively charged sodium ions from the tubule 354-374 to the peritubular capillary 408. This can lead to a lesser degree of sodium (and water) reabsorption. Likewise, a greater degree of sodium and water can be excreted through the ureter 106 and eventually eliminated from the body.

Thus, the application of an electric field can have a diuretic effect on the kidney. This result can potentially be of great benefit to patients who are fluid overloaded, such as heart failure patients. One problem that may develop with this approach, as with loop diuretics, is increased excretion of potassium. Because potassium ions are also positively charged (like sodium ions), applying an electric filed in the manner described above can result in decreased reabsorption of potassium. This can be dangerous because low potassium levels, or hypokalemia, can result in cardiac arrhythmias, severe muscle weakness or paralysis, rhabdomyolysis, and renal dysfunction. Thus, in certain examples, the application of electric fields to the kidney can be accompanied by a potassium monitoring and a feedback control mechanism, as described below, such that hypokalemia is avoided. Alternatively, this therapy can be used with increased potassium intake (through pills), or other potassium sparing diuretics.

FIG. 5 is a block diagram illustrating an example of a monitoring circuit 118. The monitoring circuit 118, which can be an implanted or external device, can include chemical sensors 504 and 506 for constituent 1 and constituent 2, respectively. The chemical sensors can include among other things, a sodium sensor, a potassium sensor, a hydrogen ion sensor, and a bicarbonate sensor. An approach to monitoring bodily fluids with chemical sensors is described in International Patent Application PCT/US2007/068954, entitled "Implantable Medical Device with Chemical Sensor and Related Methods," which is incorporated herein by reference in its entirety. Chemical sensors 504 and 506 can detect a physiological level or concentration of a constituent, such as an ion, in a bodily fluid of a subject (e.g. blood, interstitial fluid, serum, lymph, and serous fluid). Chemical sensors 504 and 506 can each include an optical excitation assembly 508, 510; a sensing element 512, 514; and an optical detection assembly 516, 518. Furthermore, chemical sensors 504 and 506 can be communicatively linked through wired or wireless technologies.

The monitoring circuit 118 is coupled to the controller circuit 116, as shown in FIG. 1. Thus, when the monitoring circuit 118 detects the levels of the first and second constituent, these values can be communicated to the controller circuit 116. In certain examples, the controller circuit 116 can use these values to determine whether a given level of constituent 1 or constituent 2 is within a predetermined range. If the level of the first constituent is above or below a predetermined range, the controller circuit 116 can modulate the electric field by increasing or decreasing a magnitude, pulsewidth, frequency, duration, or waveform associated with the electric field. Similarly, if the level of the second constituent is above or below a normal physiological range, the controller circuit 116 can modulate the electric field by increasing or decreasing a magnitude, pulsewidth, frequency, duration, or waveform associated with the electric field. For example, if chemical sensor 504 detects an abnormally high level of sodium, this information can be communicated to the controller circuit 116, which can control the electric field by increasing the strength, duration, or frequency, for example, thereby affecting the electrophoretic gradient for sodium, causing decreased reabsorption, increased excretion, and ultimately a decrease in the level of sodium detected by chemical sensor 504. In another example, chemical sensor 506 can detect an abnormally low level of potassium. This information can trigger the controller circuit to decrease the strength, duration, or frequency of the electric field, for example, thereby affecting the electrophoretic gradient for potassium, causing increased reabsorption and decreased excretion of potassium (and sodium), and ultimately leading to an increase in the level of potassium detected by chemical sensor 504. From these examples, it is apparent that the electric field must be tightly controlled in such a manner as to effectuate the removal of sodium while at the same time maintaining a normal physiological level of potassium. The monitoring circuit 118 can be used to help achieve the necessary control of the electric field.

Additional Notes

In this document, certain examples have been described with respect to "sodium" and "potassium" levels for illustrative clarity. The terms "sodium" and "potassium," as used in this document, can be used to refer to "sodium ions" and "potassium ions," respectively, without departing from the scope of the described systems or methods. Similarly, the terms "sodium" and "salt," as used in this document, can be used interchangeably to refer to "sodium ions" without departing from the scope of the described systems or methods.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
    a first electrode and a second electrode, wherein at least one of the first electrode or the second electrode is implantably associated with a kidney of a subject;
    an electric field generator circuit coupled to the first electrode and the second electrode and configured to generate an electric field; and
    a controller circuit coupled to the electric field generator circuit and configured to control the electric field between the first and second electrodes, such that, through a process of electrophoresis, an electrophoretic gradient is produced to cause a net migration of a first constituent from a peritubular capillary of the kidney to a tubule associated with the peritubular capillary, wherein the first constituent is removed from the subject and a second constituent is maintained within a specified physiological range.

2. The system of claim 1, further comprising a monitoring circuit configured to monitor a level of the first constituent in the kidney and a level of the second constituent in the kidney.

3. The system of claim 1, wherein the first electrode includes a cathode and is located in or near at least one of a Bowman's capsule, a macula densa, a tubule, a collecting duct, a renal pelvis, a ureter, or a urinary bladder.

4. The system of claim 1, wherein the second electrode includes an anode and is located in or near at least one of a renal vein, a renal artery, or a peritubular capillary network.

5. The system of claim 1, wherein the first constituent includes sodium and the second constituent includes potassium.

6. The system of claim 1, wherein the controller circuit is configured to control the electric field to remove water from the kidney.

7. The system of claim 6, wherein the controller circuit is configured to control the electric field to treat a condition of the subject including fluid overload.

8. The system of claim 1, wherein the electric field generator circuit is configured to generate a biphasic voltage pulse comprising a first and a second phase, a magnitude of at least one of the first or the second phase being between about 0.1 Volt and about 20 Volts.

9. The system of claim 1, wherein the electric field generator circuit is configured to generate pulses at a repetition rate that is between about 10 minutes and about 1 microsecond.

10. The system of claim 1, wherein the controller circuit is configured to control at least one of a magnitude, a pulsewidth, a frequency, a duration, or a waveform associated with the electric field using information about at least one of the level of the first or the second constituent.

11. The system of claim 1, wherein the controller circuit is configured to control at least one of a magnitude, a pulsewidth, a frequency, a duration, or a waveform associated with the electric field using information from at least one implanted sensor including an implantable heart sound sensor; an implantable impedance sensor; an implantable activity sensor; an implantable respiration sensor; an implantable blood pressure sensor; an implantable electrocardiogram sensor; an implantable oxygen saturation sensor; an implantable blood flow sensor; an implantable temperature sensor; or an implantable renal conductivity sensor.

12. A method comprising:
applying an electric field to a subject using a first electrode and a second electrode, at least one of the first electrode or the second electrode being implantably associated with a kidney of the subject; and
controlling the electric field between the first and second electrodes, such that, through a process of electrophoresis, an electrophoretic gradient is produced to cause a net migration of a first constituent from a peritubular capillary of the kidney to a tubule associated with the peritubular capillary, wherein the first constituent is removed from the subject and a second constituent is maintained within a specified physiological range.

13. The method of claim 12, further comprising monitoring a level of the first constituent in the kidney and a level of the second constituent in the kidney.

14. The method of claim 12, wherein the applying an electric field includes using the first electrode, including a cathode, in or near at least one of a Bowman's capsule, a macula densa, a tubule, a collecting duct, a renal pelvis, a ureter, or a urinary bladder.

15. The method of claim 12, wherein the applying an electric field includes using the second electrode, including an anode, in or near a renal vein, a renal artery, or a peritubular capillary network.

16. The method of claim 12, wherein the first constituent includes sodium and the second constituent includes potassium.

17. The method of claim 12 wherein the controlling the electric field includes removing water from the kidney.

18. The method of claim 17, wherein the removing the water from the kidney includes to treat a condition of the subject including fluid overload.

19. The method of claim 12, wherein the applying an electric field includes providing a biphasic voltage pulse including a first and a second phase, a magnitude of at least one of the first or the second phase being between about 0.1 Volt and about 20 Volts.

20. The method of claim 12, wherein the applying an electric field includes providing pulses at a repetition rate that is between about 10 minutes and about 1 microsecond.

21. The method of claim 12, wherein the controlling the electric field includes controlling at least one of a magnitude, a pulsewidth, a frequency, a duration, or a waveform associated with the electric field using information about at least one of the level of the first constituent or the second constituent.

22. The method of claim 12, wherein the controlling the electric field includes controlling at least one of a magnitude, a pulsewidth, a frequency, a duration, or a waveform associated with the electric field using information from at least one implanted sensor including an implantable heart sound sensor; an implantable impedance sensor; an implantable activity sensor; an implantable respiration sensor; an implantable blood pressure sensor; an implantable electrocardiogram sensor; an implantable oxygen saturation sensor; an implantable blood flow sensor; an implantable temperature sensor; or an implantable renal conductivity sensor.

* * * * *